United States Patent
Young et al.

(10) Patent No.: US 11,000,334 B1
(45) Date of Patent: May 11, 2021

(54) SYSTEMS AND METHODS FOR MODELING SPINES AND TREATING SPINES BASED ON SPINE MODELS

(71) Applicant: K2M, Inc., Leesburg, VA (US)

(72) Inventors: Anthony Young, Annandale, VA (US); Margaret Redford, Isle Of Palms, SC (US); Jennifer McCool, Boyce, VA (US); John Schmidt, Bluemont, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/648,086

(22) Filed: Jul. 12, 2017

(51) Int. Cl.
*A61B 34/10* (2016.01)
*A61B 6/00* (2006.01)
(Continued)

(52) U.S. Cl.
CPC .............. *A61B 34/10* (2016.02); *A61B 6/505* (2013.01); *A61B 6/5294* (2013.01); *A61B 6/563* (2013.01); *A61B 17/7002* (2013.01); *A61B 17/7059* (2013.01); *A61F 2/30942* (2013.01); *A61F 2/32* (2013.01); *A61F 2/38* (2013.01); *A61F 2/4202* (2013.01); *A61F 2/442* (2013.01); *B33Y 50/00* (2014.12); *G05B 19/4099* (2013.01);
(Continued)

(58) Field of Classification Search
CPC .. A61B 17/703; A61F 2/3094; A61F 2/30942; A61F 2002/30943; A61F 2002/30948; A61F 2002/30952; A61F 2002/30955
See application file for complete search history.

(56) References Cited

U.S. PATENT DOCUMENTS

| 7,657,072 B2 | 2/2010 | Periaswamy et al. |
| 8,527,244 B2 | 9/2013 | Shin |

(Continued)

FOREIGN PATENT DOCUMENTS

| WO | 9959106 A1 | 11/1999 |
| WO | 2017027873 A1 | 2/2017 |

OTHER PUBLICATIONS

International Search Report for PCT/US2018/041831 dated Nov. 19, 2018.
(Continued)

*Primary Examiner* — Lynnsy M Summitt
*Assistant Examiner* — Christina Negrellirodriguez
(74) *Attorney, Agent, or Firm* — Howard & Howard Attorneys PLLC

(57) ABSTRACT

Systems and methods for performing surgery based on an analysis of images captured in at least two different planes are disclosed. According to some embodiments, a first X-ray image of a spine in a first plane and a second X-ray image of the spine in a second plane are obtained, and a curve is drawn on the first and second X-ray images so that the curve tracks the vertebral bodies of the spine. The coordinates of the curve in the first and second X-ray images are determined by performing image processing to detect the curve in the X-ray images. A three-dimensional model of the spine is constructed based on the coordinates. The model is analyzed based on medical data relating to the spine and models of other spines to determine parameters of a spinal device. The spinal device is constructed and deployed in the spine based on the parameters.

19 Claims, 12 Drawing Sheets

(51) Int. Cl.

| | | |
|---|---|---|
| *A61B 17/70* | (2006.01) | |
| *A61F 2/44* | (2006.01) | |
| *A61F 2/32* | (2006.01) | |
| *A61F 2/38* | (2006.01) | |
| *A61F 2/42* | (2006.01) | |
| *A61F 2/30* | (2006.01) | |
| *G06T 15/08* | (2011.01) | |
| *G06T 7/246* | (2017.01) | |
| *G05B 19/4099* | (2006.01) | |
| *B33Y 50/00* | (2015.01) | |
| *G16H 50/50* | (2018.01) | |
| *A61F 2/46* | (2006.01) | |
| *G06F 19/00* | (2018.01) | |

(52) U.S. Cl.
CPC .............. *G06T 7/251* (2017.01); *G06T 15/08* (2013.01); *G16H 50/50* (2018.01); *A61B 2034/104* (2016.02); *A61B 2034/105* (2016.02); *A61B 2034/108* (2016.02); *A61F 2002/30952* (2013.01); *A61F 2002/30953* (2013.01); *A61F 2002/4633* (2013.01); *G05B 2219/49023* (2013.01); *G06F 19/321* (2013.01); *G06T 2207/10024* (2013.01); *G06T 2207/10116* (2013.01); *G06T 2207/20221* (2013.01); *G06T 2207/30012* (2013.01)

(56) References Cited

U.S. PATENT DOCUMENTS

| | | |
|---|---|---|
| 9,393,130 B2 | 7/2016 | Suddaby et al. |
| 9,408,638 B2 | 8/2016 | Kroll et al. |
| 9,561,004 B2 | 2/2017 | Forsberg |
| 9,566,163 B2 | 2/2017 | Suddaby et al. |
| 9,572,601 B2 | 2/2017 | Stenulson et al. |
| 9,585,762 B2 | 3/2017 | Suddaby et al. |
| 2009/0232378 A1 | 9/2009 | Nakamura |
| 2011/0295378 A1 | 12/2011 | Bojarski et al. |
| 2014/0228860 A1* | 8/2014 | Steines ............... A61F 2/30942 606/130 |
| 2014/0323845 A1 | 10/2014 | Forsberg |
| 2015/0328004 A1 | 11/2015 | Mafhouz |
| 2016/0022323 A1 | 1/2016 | Seme et al. |
| 2016/0166396 A1 | 6/2016 | McClintock |
| 2016/0317187 A1 | 11/2016 | Seme et al. |
| 2017/0228896 A1 | 8/2017 | Yu et al. |

OTHER PUBLICATIONS

Huynh KT, Gibson I, Gao Z. Development of a detailed human spine model with haptic interface. InHaptics Rendering and Applications 2012. InTech. Uploaded by Ian Gibson May, 21, 2014, 31 pages.

International Search Report including Written Opinion for PCT/US2018/053743 dated Dec. 21, 2018.

* cited by examiner

SYSTEMS AND METHODS FOR MODELING SPINES AND TREATING SPINES BASED ON SPINE MODELS

BACKGROUND

1. Technical Field

This disclosure pertains generally to modeling aspects of the human skeleton, and more particularly to developing and using models of a spine and using other medical data relating to the spine to customize spinal devices and the methods of performing spinal surgery so as to result in a desired outcome, such as a balanced spine.

2. Discussion of Related Art

Today a wide-variety of surgical devices and software are being developed and used to perform various spinal surgical procedures. In many spine surgeries, surgical devices and software are used to correct a patient's spine so that the skull is oriented over or aligned with the pelvis. Specifically, the surgical devices and software are used to ensure that the vertebral bodies are in normal sagittal alignment so that there is a gradual transition of curvatures from cervical lordosis, to thoracic kyphosis, to lumber lordosis. Although such spinal surgery may result in normal sagittal alignment of the spine, the spine may not be properly aligned in the coronal plane and further surgery may be needed to make a correction.

SUMMARY

The present disclosure features systems and methods for constructing a three-dimensional model of the curvature of a boney structure such as a spine based on images of the bony structure captured in at least two different planes, and using that model and medical data relating to the bony structure, e.g., osteoporosis, to predict postoperative changes in the curvature of the bony structure. The images of the bony structure may be captured by any type of medical imaging apparatus such as an X-ray apparatus, a magnetic resonance imaging (MM) apparatus, or a computed tomography (CT) scanner. According to embodiments of the present disclosure, a medical device such as a spinal device may then be designed to counter or otherwise address the predicted postoperative changes in the curvature of the bony structure such as the spine so that proper alignment of the bony structure may be achieved.

In aspects, the present disclosure features a method which includes obtaining or acquiring a first X-ray image of at least a portion of a spine in a first plane and obtaining or acquiring a second X-ray image of the at least a portion of a spine in a second plane. The method also includes drawing, on the first X-ray image and the second X-ray image, a line or curve that passes through vertebral bodies of at least a portion of a spine, and constructing a three-dimensional model based on the lines or curves drawn on the first and second X-ray images. The method further includes determining parameters of a spinal device based on the three-dimensional model and deploying the spinal device on or near the spine based on the three-dimensional model.

In some aspects, the spinal device is a screw, a rod, a cervical plate, a spine implant, an interbody device, or an artificial disc.

In some aspects, the first plane is a coronal plane and the second plane is a sagittal plane.

In some aspects the method further includes obtaining a third X-ray image of at least a portion of the spine in an axial plane. In aspects, constructing the three-dimensional model includes constructing the three-dimensional model based on the lines or curves drawn on the first, second, and third X-ray images.

In some aspects, the method further includes identifying a line or curve on the first X-ray image and identifying a line or curve on the second X-ray image.

In some aspects, the lines are colored lines, and identifying the colored line includes quantifying the color of the colored lines and identifying differences in characteristics of the colored lines. In those aspects, the color of the colored lines includes at least one of Red, Green, or Blue, and the characteristics include at least one of intensity, hue, saturation, contrast, or brightness.

In some aspects, the method further includes calibrating the first X-ray image and the second X-ray image.

In some aspects, the method further includes obtaining coronal y-z coordinates or pixels of a central vertebral line with vertebral bodies and discs identified, and obtaining sagittal x-z coordinates or pixels.

In some aspects, the method further includes compensating for differences in magnification between the first X-ray image and the second X-ray image, and scaling the first and second X-ray images.

In some aspects, the method further includes combining the first and second X-ray images to construct the three-dimensional model.

In some aspects, the method further includes obtaining at least one four-dimensional model for a similar spine, analyzing the three-dimensional model based on at least one four-dimensional model to predict movement of the spine, and determining the parameters of the spinal device based on the predicted movement of the spine. In aspects, the similar spine is an abnormal spine, and the spine is a one-level degenerative disc case and the similar spine is a two-level degenerative disc case.

In some aspects, the method further includes acquiring medical data regarding a patient, analyzing the three-dimensional model in view of the medical data to predict movement of the spine over time, and determining the parameters of the spinal device based on the predicted movement of the spine.

In some aspects, the medical data includes at least one of diagnosis information, operative information, follow-up information, quality of life score, cardio information, diabetes information, or intra-operative information.

In some aspects, the quality of life score is selected from the group consisting of Visual Analog Scale (VAS), Oswestry Disability Index (ODI), Neck Disability Index, Rowland-Morris, Short Form Health Survey-12, Short Form Health Survey-36, Scoliosis Research Society-36 (SRS36), and Scoliosis Research Society-22 (SRS-22).

In some aspects, the method further includes generating instructions to construct the spinal device with a three-dimensional printer based on the parameters of the spinal device.

In aspects, the present disclosure features a method for performing spinal surgery. The method includes obtaining, over a predetermined period, a plurality of first images (e.g., X-ray or other images) of at least a portion of a first spine in a first plane, and obtaining, over a predetermined period, a plurality of second images of the at least a portion of the first spine in a second plane. The method further includes drawing a line that passes through vertebral bodies of the at least a portion of the first spine in the plurality of first images and in the plurality of second images, acquiring medical data relating to the first spine, constructing a four-dimensional model based on the lines drawn on the pluralities of first and second images, analyzing the four-dimensional model in view of the medical data to predict movement of the first spine over time, obtaining medical data relating to the first spine, determining parameters of a spinal device based on the four-dimensional model and the obtained medical data, and deploying the spinal device in a second spine.

In aspects, the present disclosure features still another method of performing a surgical procedure. The method includes obtaining, over a predetermined period, a plurality of first images of a first plurality of skeletal bodies in a first plane, obtaining, over a predetermined period, a plurality of second images of the first plurality of skeletal bodies in a second plane, drawing a line through the first plurality of bony structures or skeletal bodies in the pluralities of first and second images, constructing a four-dimensional model based on the lines drawn on the pluralities of first and second images, determining parameters of a medical device based on the four-dimensional model, forming a medical device based on the determined parameters; and applying the medical device to at least one skeletal body of a second plurality of skeletal bodies.

In some aspects, the method includes the first and second pluralities of bony structures or skeletal bodies include bones of and/or associated with a hip, knee, or ankle.

In aspects, the present disclosure features a system for manufacturing a spinal device. The system includes a server, an X-ray apparatus, a computer, and a three-dimensional printer or milling machine. The server stores medical data. The X-ray apparatus captures a first X-ray image of a spine in a first plane and a second X-ray image of the spine in a second plane, and stores the first and second X-ray images in the server.

The computer includes a communications interface, one or more processors coupled to the communications interface, and a memory coupled to the one or more processor and having stored thereon instructions which, when executed by the one or more processors, causes the one or more processors to acquire via the communications interface the first X-ray image of the spine in the first plane and the second X-ray image of the spine in the second plane from the server, store the first and second X-ray images in the memory, acquire medical data relating to the spine from the server, store the medical data in memory, draw, on the first X-ray image and the second X-ray image, a curve through vertebral bodies of the spine, determine coordinates of the spine by detecting the curve on the first X-ray image and the second X-ray image, construct a three-dimensional model based on the curves on the first and second X-ray images, predict movement of the spine during a postoperative period based on the three-dimensional model and the medical data, which includes three-dimensional models of other spines, determine parameters of a spinal device based on the predicted movement of the spine, and transmit via the communications interface commands or instructions for forming a surgical device having the determined parameters.

The three-dimensional printer or milling machine acquires the commands or instructions and forms the surgical device based on the commands or instructions.

BRIEF DESCRIPTION OF THE DRAWINGS

Various aspects of the present disclosure are described hereinbelow with reference to the drawings, wherein.

DETAILED DESCRIPTION

Figure 1:
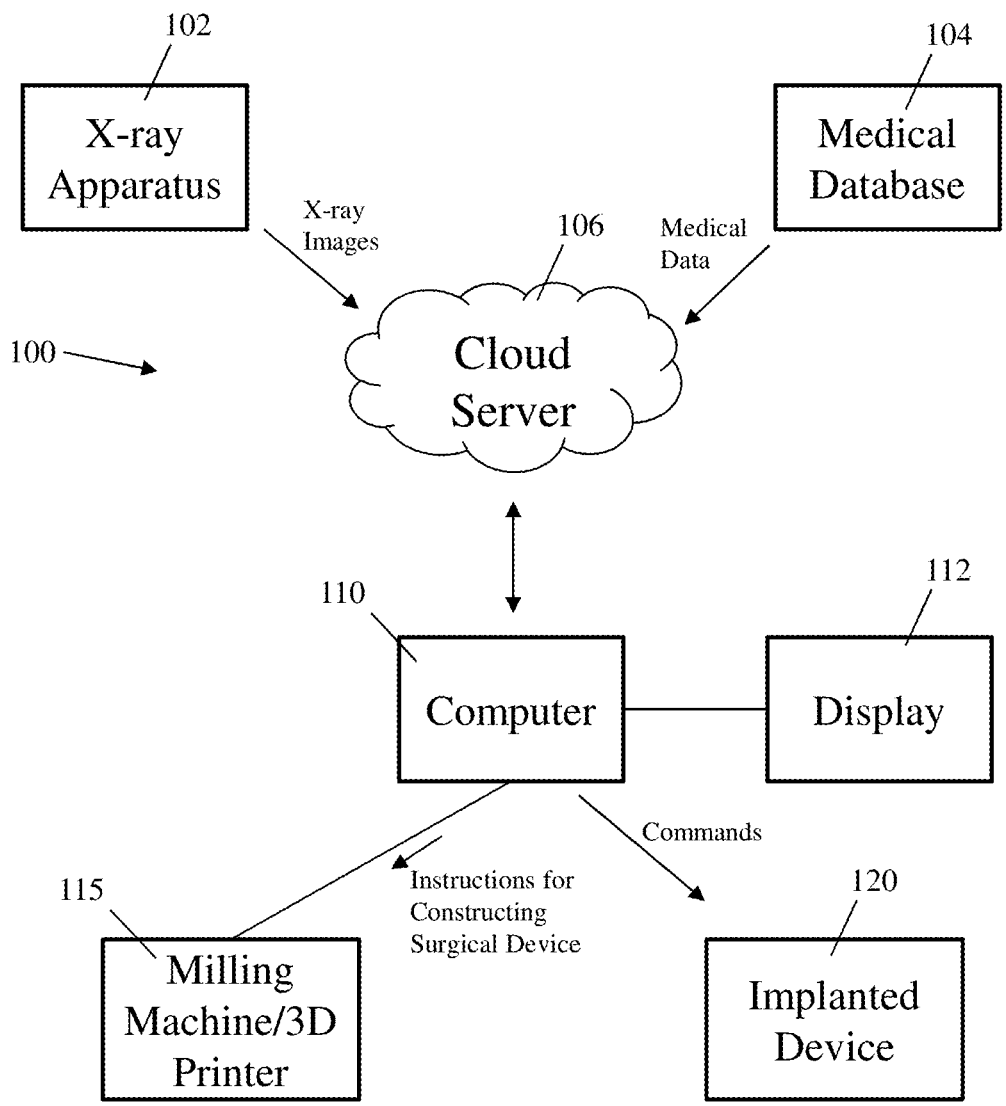
FIG. 1 is a block diagram illustrating a system architecture for performing spinal imaging, analysis, and surgery in accordance with some embodiments.

Embodiments of the present spine modeling systems and methods are now described in detail with reference to the drawings in which like reference numerals designate identical or corresponding elements in each of the several views. As used herein, the term "clinician" refers to a doctor, a nurse, or any other care provider and may include support personnel. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so.

As used herein, the term "sagittal plane" refers to a plane that divides the body into left and right halves and is parallel to an x-axis, the term "coronal plane" refers to a plane that divides the body into front and back (or posterior and anterior) portions and is parallel to a y-axis, the term "height" refers to a distance along a z-axis.

The goal of some spinal surgeries and the spinal devices that are used in those surgeries is to correct a spine so that it is in "sagittal balance." In short, sagittal balance means that the skull is positioned over or aligned with the pelvis. Many surgeons use software to guide them through the surgical procedure to ensure that "sagittal balance" is achieved. In some cases, while the surgeon may successfully place the spine in "sagittal balance," the spine may not be in "coronal balance" or, after the surgery, the spine may shift out of "coronal balance."

According to embodiments of the present disclosure, the position of the spine and skull are quantified in three-dimensional space by performing image processing and analysis on at least sagittal and coronal X-rays of the spine. The resulting three-dimensional model of the curvature of the spine may be compared to three-dimensional models of the curvature of other spines and analyzed in view of medical data related to the spine to determine an appropriate treatment plan to ensure both sagittal and coronal balance. The treatment plan may include constructing a surgical device and deploying it in, on, or near the spine based on the analysis of the three-dimensional model of the target spine.

FIG. 1 is a block diagram illustrating an examplary system architecture for performing spinal imaging, analysis, and surgery in accordance with some embodiments. In some embodiments, an X-ray apparatus 102 provides X-ray images to a cloud server 106. The cloud server 106 may be secured in such a way that it complies with the privacy protection provisions of the Health Insurance Portability and Accountability Act of 1996 (HIPAA). In other embodiments, the X-ray apparatus 102 provides X-ray images to a computer or a server that may better protect patient information than cloud server 106. The X-ray apparatus 102 may be any X-ray apparatus that is configured to capture X-ray images of the human skeleton. The system architecture 100 may also include a medical database 104 that transmits and stores medical data in the cloud computer or server 106. The medical database 104 may reside in a doctor's office or in a hospital and may contain a variety of medical data that is useful in determining the method of performing spinal surgery and the parameters of the spinal device that is used to correct the misalignment of the spine. This medical data may include all medical conditions that are or may be relevant to the spine, including, for example, osteoporosis, adolescent idiopathic scoliosis, adult scoliosis, neuromuscular disease, and degenerative disc disease. In embodiments, the medical data may include one or more of the following: patient demographics, progress notes, vital signs, medical histories, human clinical data, diagnoses, medications, Cobb Angle measurements, adverse events, operative complications, implant complications, operative time, blood loss, immunization dates, allergies, X-ray images, such as coronal and sagittal X-ray images, and lab and test results.

Cloud computer server 106 may store the X-ray images and medical data in a way to allow for easy access by computer 110 that has access to the cloud computer or server 106. Computer 110 may display the X-ray images and the medical data to assist a clinician in planning for and performing a spinal surgery. Based on the X-ray images and the medical data, computer 110 may analyze X-ray images in the medical data to determine an appropriate method of performing a spinal surgery and/or the parameters of the medical device to ensure that proper alignment is achieved well after the spinal surgery is performed.

The computer 110 may then analyze the X-ray images and the medical data to determine instructions for constructing a surgical device or spinal device using milling machine or three-dimensional printer 115. Alternatively or additionally, computer 110 may determine commands to send via a wireless communications link to a device that is implanted in, on, or near a spine. The commands may include a command to activate a motor to change a dimension of the implanted surgical device to change the position of at least a portion of the spine.

Figure 2:
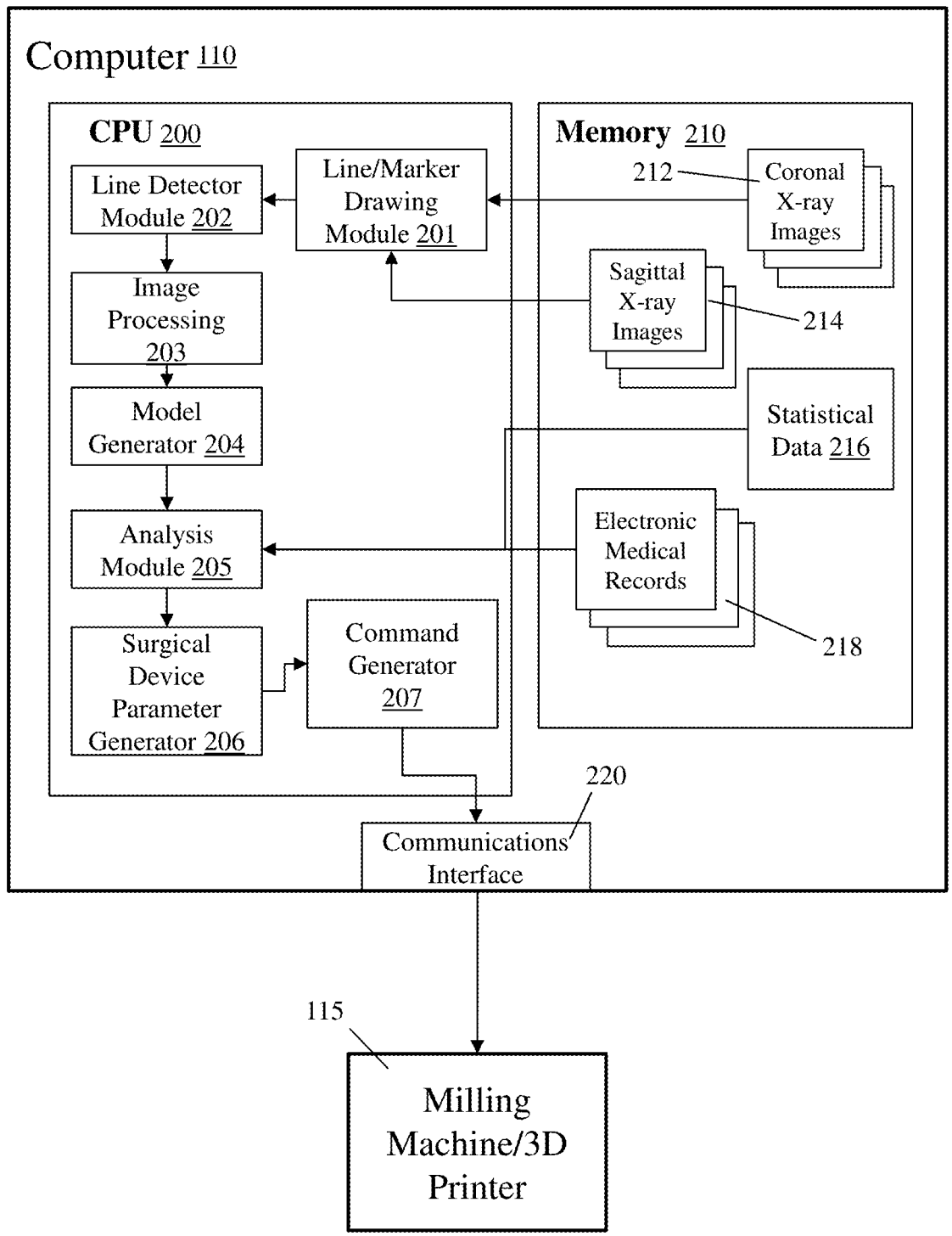
FIG. 2 is a block diagram illustrating a computer and surgical device manufacturing machine employed in the system architecture of FIG. 1.

FIG. 2 is a block diagram illustrating computer 110 coupled to milling machine/three-dimensional printer 115 employed in the system architecture 100 of FIG. 1. Computer 110 includes central processing unit 200 and memory 210. In some embodiments, a portion of the X-ray images stored in cloud server 106 are retrieved from the cloud server 106 by computer 110 and stored in memory 210. The X-ray images retrieved from cloud server 106 may include coronal X-ray images 212 and sagittal X-ray images 214 of one or more spines. Computer 110, under the control of the central processing unit 200, may also retrieve electronic medical records 218 from cloud server 106. Memory 210 may also store statistical data 216 that may be useful in analyzing coronal and sagittal X-ray images 212, 214, and electronic medical records 218.

Components of the system of the present disclosure can be embodied as circuitry, programmable circuitry configured to execute applications such as software, communication apparatus applications, or as a combined system of both circuitry and software configured to be executed on programmable circuitry. Embodiments may include a machine-readable medium storing a set of instructions which cause at least one processor to perform the described methods. Machine-readable medium is generally defined as any storage medium which can be accessed by a machine to retrieve content or data. Examples of machine readable media include but are not limited to magneto-optical discs, read only memory (ROM), random access memory (RAM), erasable programmable read only memories (EPROMs), electronically erasable programmable read only memories (EEPROMs), solid state communication apparatuses (SSDs) or any other machine-readable device which is suitable for storing instructions to be executed by a machine such as a computer.

In operation, the CPU 200 executes a line or marker drawing module 201 that retrieves the coronal X-ray images 212 and the sagittal X-ray images 214, and draws a line through the vertebral bodies of the spines shown in the coronal X-ray images 212 and the sagittal X-ray images 214. The line or marker drawing module 201 may also place markers on the spine to show different segments of the spine or to show inflection points on the spine. As is described in more detail below, the CPU 200 next executes a line detector module 202 that detects and determines the coordinates of the line drawn on each of the coronal X-ray images 212 and the sagittal X-ray images 214.

Next, the CPU 200 executes image processing 203 to scale or otherwise modify the coronal X-ray images 212 and the sagittal X-ray images 214 so that the lines or curves corresponding to the spine, and the coronal and sagittal X-ray images 212, 214 are scaled correctly with respect to each other so that they may be combined with each other into a three-dimensional or four-dimensional model of one or more spines.

The central processing unit 200 also executes a model generator 204. The model generator 204 takes the line or curve information and generates a three-dimensional model of the deformed spine. The central processing unit 210 then executes an analysis module 205 that analyzes one or more of statistical data 216, electronic medical records 218 retrieved from memory 210, and the three-dimensional or four-dimensional models generated by the model generator 204 to determine or predict postoperative changes in the curvature of the spine.

The central processing unit 200 also includes a surgical device parameter generator 206. The surgical device parameter generator 206 uses the determined or predicted postoperative changes in the spine to determine parameters of a surgical device, such as a spinal implant, that can counter the predicted postoperative changes in the spine to ensure proper alignment of the spine postoperatively. The central processing unit 200 may optionally include a command generator 207 for generating commands or instructions for controlling the milling machine or three-dimensional printer 115 to form or construct surgical device according to the parameters generated by the surgical device parameter generator 206. The computer 110 also includes a communications interface 220 that is in communication with the milling machine or three-dimensional printer 115 to provide commands or instructions to the milling machine or three-dimensional printer 115.

Figure 3:
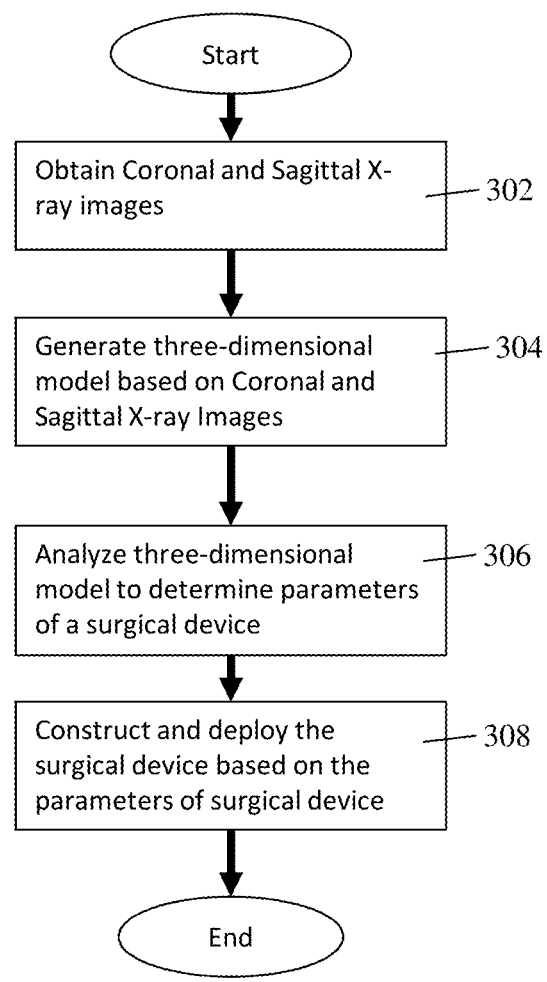
FIG. 3 is a flow diagram illustrating a process for performing a spinal surgery in accordance with some embodiments.

FIG. 3 is a flow diagram illustrating a process for performing spinal surgery in accordance with some embodiments. After starting, the coronal and sagittal X-ray images are obtained from a cloud computer or other similar database at block 302. The coronal and sagittal X-ray images may be X-ray images of a spine and may be obtained prior to the surgical procedure. The X-ray images may also include images that were obtained both before and after a previous surgical procedure, e.g., a procedure performed on the spine.

At block 304, a three-dimensional model is generated based on coronal and sagittal X-ray images. In embodiments, the resolution of the of the X-ray images is greater than the variation in size of the implants. For example, the resolution of the X-ray images may be 0.4 mm, while the implants may come in sizes with 1 mm variation. As described in more detail below, the coronal and sagittal X-ray images are analyzed to determine coordinates of the spine in three-dimensional space. In other words, X-ray images are processed to generate three dimensions, e.g., length, width, and height in millimeters.

At block 306, the three-dimensional model is analyzed to determine parameters of a surgical device and/or steps for performing a spinal procedure. The analysis may include comparing the three-dimensional model to three-dimensional models of similarly-situated patients. For example, if the X-ray images of similarly-situated patients show a change in position or curvature of portions of the spine in a direction away from normal alignment after a surgical procedure to align the spine, it may be determined that the parameters or dimensions of the surgical device need to be adjusted to account for this change in position or movement.

At block 308, the surgical device is constructed and deployed at or near the spine based on the parameters of the surgical device determined based on an analysis of at least the three-dimensional model of the spine of the target patient. For example, the surgical device may be formed using a milling machine by inserting an object in the milling machine and providing instructions to the milling machine to remove material from the object to form a surgical device according to the parameters or dimensions determined during the analysis of the three-dimensional model.

Figure 4:
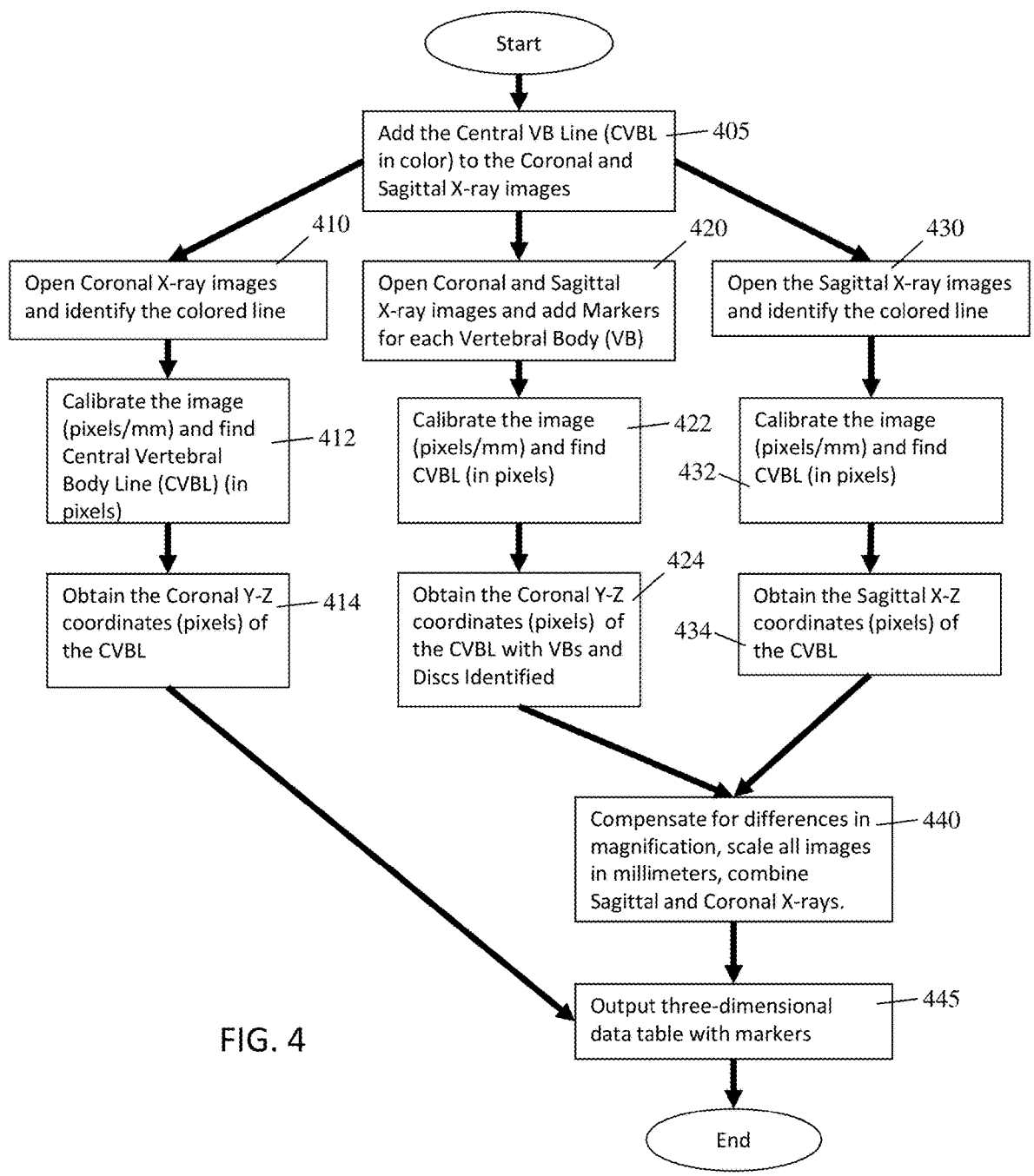
FIG. 4 is a flow diagram illustrating an example process for generating a model of a spine in the process of FIG. 3.

FIG. 4 is a flow diagram illustrating an examplary process for generating a model of a spine in the process of FIG. 3. At block 405, a line or curve is drawn on or superimposed on the vertebral bodies of the spine shown in the coronal and sagittal X-ray images. The curve or line, also referred to as a central vertebral body line, may be one color or a combination of colors. The color of the curve or line may be selected to optimize the detection of the curve or line superimposed on the coronal and sagittal X-ray images.

At block 410, the coronal X-ray images are opened and the colored lines or curves are identified or detected. This may be done by quantifying the color of the line or curve and search for differences in red, green, blue, intensity, hue, saturation, contrast, and/or brightness to identify or detect the central vertebral body line on the coronal X-ray image. For example, for a standard 36-inch X-ray, such a detection process may result in between 2500 and 3000 data points for the line or curve. The final number of data points is determined by the size of the image. In this way, the curvature of the spine is constructed and not the vertebral bodies themselves. Consequently, the three-dimensional models of the curvature of spines may be stored in memory using a small amount of memory resources. At step 412, the coronal X-ray images are calibrated and the central vertebral body line is found.

At block 420, the coronal and sagittal markers for each vertebral body are added to the images. At block 422, the images are calibrated and the central vertebral body line is found. Then, at block 424, the coronal and sagittal coordinates or pixels of the central vertebral body lines with the vertebral bodies and discs identified are obtained.

At block 430, the sagittal X-ray images are opened and the colored lines or curves superimposed or drawn on the sagittal X-ray images are detected in the same manner as in block 410. At step 432, the coronal X-ray images are calibrated and the central vertebral body line is found. Then, in step 434, sagittal X-Z coordinates or pixels of the central vertebral body line are obtained. At block 440, the coronal Y-Z coordinates and the sagittal X-Z coordinates are compensated for differences in magnification are scaled. Then, the sagittal and coronal X-rays are combined. At block 445, a three-dimensional data table with markers are output.

Figure 5:
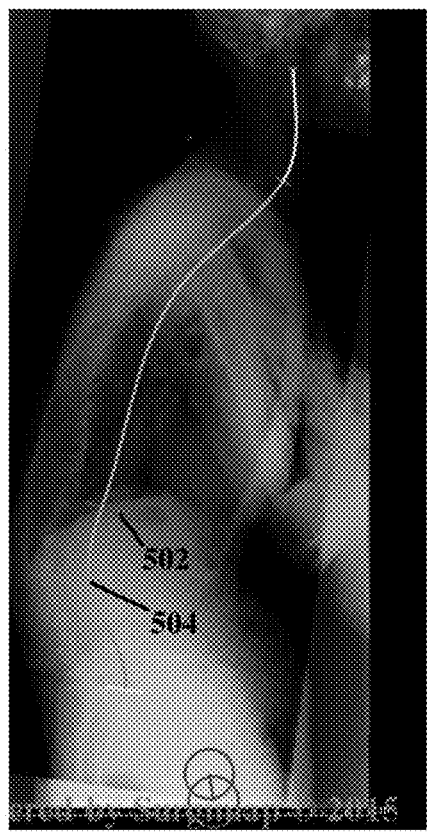
FIG. 5 is an X-ray image of a sagittal view of a preoperative spine illustrating the drawing of a curve that passes through the vertebral bodies of the preoperative spine in accordance with some embodiments.

FIG. 5 is a user interface illustrating the drawing of a curve through the vertebral bodies of a preoperative spine in a sagittal X-ray image in accordance with some embodiments. The central vertebral body curve or line 504 shows that the preoperative spine is not in proper alignment. Markers 502 indicate different portions of the spine.

Figure 6:
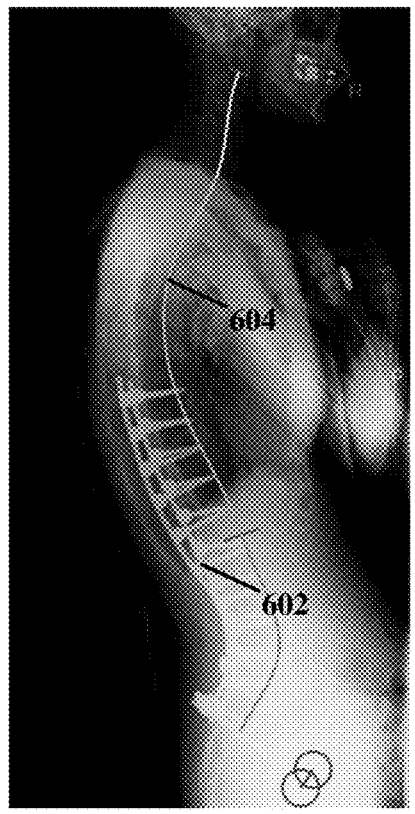
FIG. 6 is an X-ray image of a sagittal view of a postoperative spine illustrating the drawing of a curve that passes through the vertebral bodies of the postoperative spine corresponding to the preoperative spine of FIG. 5 in accordance with some embodiments.

FIG. 6 is a user interface illustrating the drawing of a curve through the vertebral bodies of a postoperative spine corresponding to the preoperative spine of FIG. 5 in accordance with some embodiments. The central vertebral body curve or line 604 shows that the postoperative spine in a sagittal X-ray image is in proper alignment because of the surgical device 602 implanted in the spine. The surgical device 602 is one of many examples of surgical devices that may be constructed and deployed in a human spine based on an analysis of the three-dimensional and four-dimensional models and medical data according to embodiments of the present disclosure.

Figure 7:
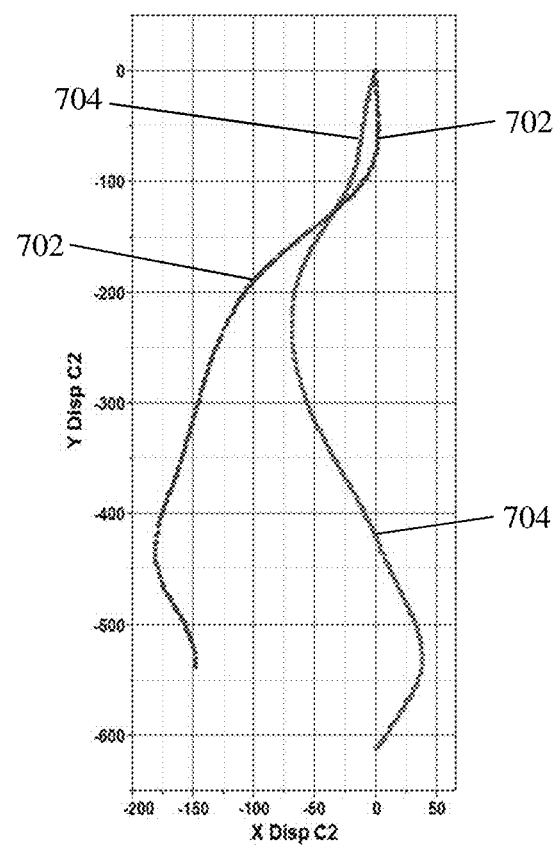
FIG. 7 is an example graph illustrating the curves extracted from the user interfaces of FIGS. 5 and 6.

FIG. 7 is an examplary graph illustrating the curves extracted from the sagittal X-ray images of FIGS. 5 and 6. Curve 702 corresponds to the curve drawn on the sagittal X-ray image of FIG. 5 and curve 704 corresponds to the curve drawn on the sagittal X-ray image of FIG. 6. Curves 702 and 704 are obtained by quantifying the color of the curves 504 and 604 drawn on the sagittal X-ray images of FIGS. 5 and 6, and finding differences in red, green, blue, intensity, hue, saturation, contrast, and brightness to identify the central sacral vertical line at every pixel. This image processing may result in thousands of data points to form curves 702 and 704.

Figure 8A:
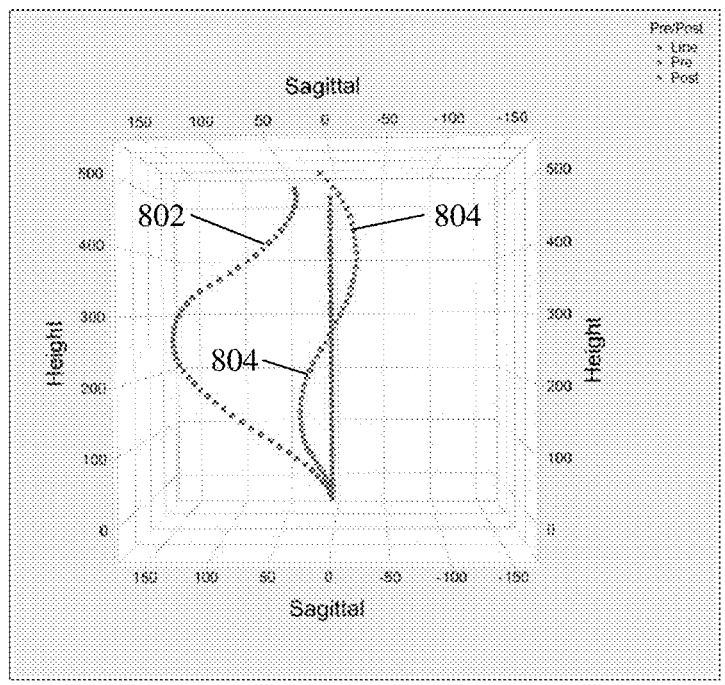
FIGS. 8A and 8B are diagrams illustrating the sagittal and coronal views, respectively, of preoperative and postoperative three-dimensional models of the curvature of a spine.
Figure 8B:
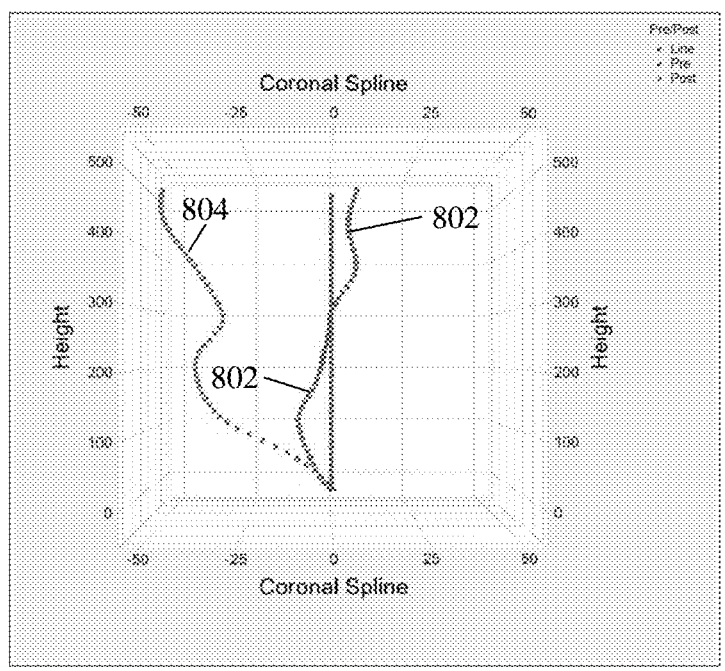

FIG. 8A is an examplary graph illustrating a three-dimensional model rotated to the sagittal view. The three-dimensional model includes a preoperative curve 802 and a postoperative curve 804. The sagittal view of FIG. 8A shows that the surgeon corrected the spine to put it in proper alignment. However, as shown in FIG. 8B, in which the three-dimensional model is rotated to the coronal view, the spine is out of balance. The postoperative curve 804 shows that the patient is leaning the patient's right. In embodiments, this information is useful in performing future spinal surgeries on the patient whose spine is illustrated in FIGS. 8A and 8B, or on other patients who have not yet undergone surgery. For example, the surgical device may be designed to counter the spine's movement to the right as shown in FIG. 8B.

Figure 9:
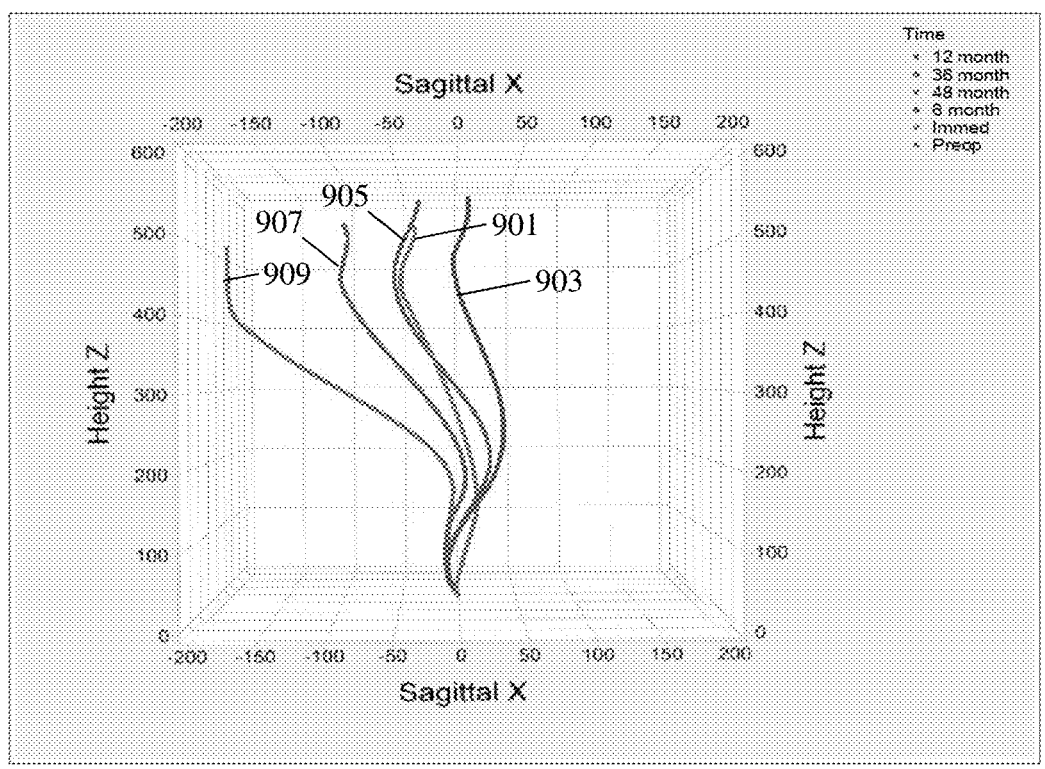
FIG. 9 is an example graph illustrating preoperative and postoperative three-dimensional models of the curvature of the spine for follow-up time periods in accordance with embodiments.
Figure 10:
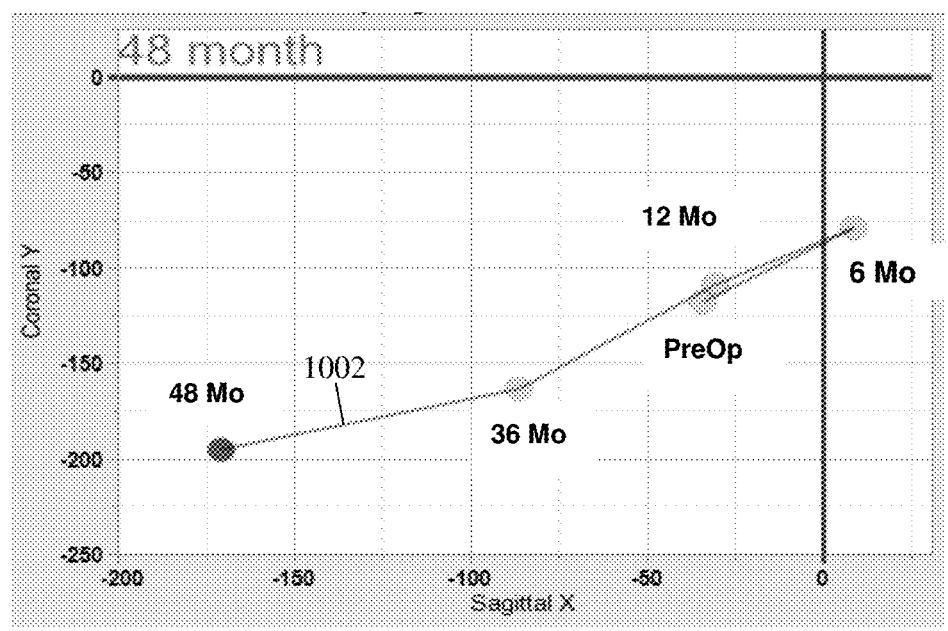
FIG. 10 is an example graph illustrating a four-dimensional model of the movement of a head from a preoperative state to a postoperative state.

FIG. 9 is an examplary graph illustrating a three-dimensional model of a spine over time from a preoperative state to a postoperative state at times 901, 903, 905, 907, 909, and FIG. 10 is an example graph illustrating a four-dimensional model of the movement of a head from a preoperative state to a postoperative state. As illustrated in FIGS. 9 and 10, the curvature of the spine, during a postoperative period, is changing from coronal and sagittal balance to an imbalanced state. In some embodiments, these models of the curvature of the spine over time may be used to predict the change in curvature of a spine of a similarly-situated patient who is being prepared for spinal-alignment surgery.

For example, as shown in FIGS. 9 and 10, the curvature of the spine that has undergone surgery is changing such that the position of the head is moving forward and to the right of a normal position of the head. If the patient of FIGS. 9 and 10 ("first patient") has similar preoperative spine positions and medical conditions as a patient who has not yet undergone a similar spinal surgery ("second patient"), the system of the present disclosure may predict that the second patient's spine will change positions in a way similar to the spine of the first patient. If there are any differences between the first and second patients, those differences may be used to adjust the predicted change in positions of the second patient's spine.

The predicted change in the positions of the second patient's spine may then be used to determine the parameters, e.g., dimensions, angles, or configurations, of the surgical device to be deployed in the second patient so as to counter the changes in positions of the second patient's spine in a case where the predicted changes in the positions of the second patient's spine results in at least one of coronal imbalance or sagittal imbalance. Once the coordinates in X-Y-Z dimensions are obtained, the determined parameters of the surgical device may be translated into instructions or commands for a milling machine or a three-dimensional printer to manufacture or form the surgical device.

Alternatively or additionally, the predicted change in the positions of the second patient's spine may be used to adjust the parameters, e.g., dimensions or configurations, of one or more adjustable surgical devices, e.g., intervertebral devices used to achieve a desired curvature of the spine, that already have been deployed in the second patient's spine. Examples of adjustable surgical devices are described in U.S. Pat. Nos. 9,585,762, 9,393,130, 9,408,638, 9,572,601, and 9,566,163, and in Pub. Nos. WO 2017/027873, US 2016/0166396, US 2016/0317187, and US 2016/0022323, the contents of each of which are hereby incorporated by reference in their entireties. Alternatively or additionally, the predicted change in the positions of the second patient's spine may be used to determine and employ appropriate surgical procedures for deploying a surgical device in the second patient's spine.

Figure 11:
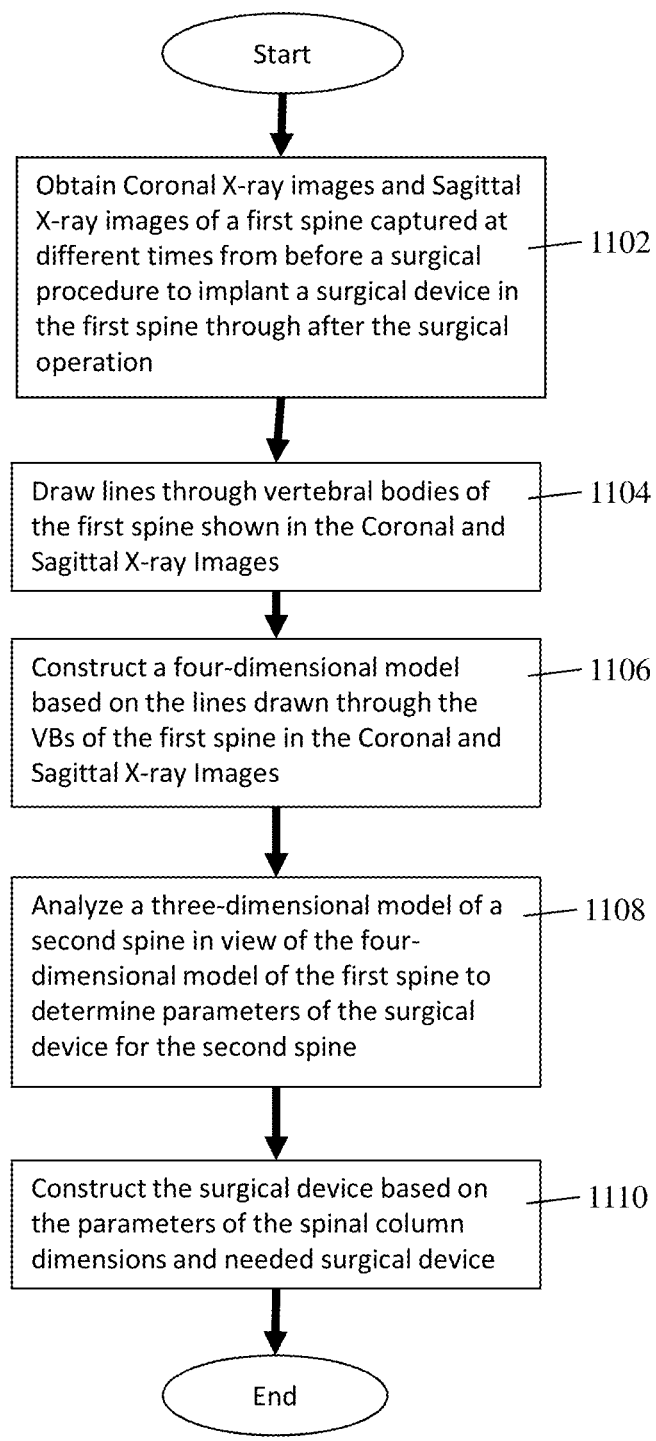
FIG. 11 is a flow diagram illustrating a process for performing spinal surgery using a four-dimensional model in accordance with some embodiments.

FIG. 11 is a flow diagram illustrating a process for performing spinal surgery using a four-dimensional model in accordance with some embodiments. At block 1102, a computer obtains coronal X-ray images and sagittal X-ray images of the first spine captured at different times. In some embodiments, the X-ray images are captured at different times during a preoperative period and during a postoperative period.

At block 1104, lines or curves are drawn through vertebral bodies of the first spine shown in the coronal and sagittal X-ray images. Specifically, image processing is applied to the coronal and sagittal X-ray images to recognize vertebral bodies and to locate a center point within the vertebral bodies through which the lines or curves may be drawn. At block 1106, a four-dimensional model is constructed based on the curves or lines drawn through the vertebral bodies of the first spine in the coronal and sagittal X-ray images. The lines or curves may be drawn by, for example, superimposing pixels of a particular color on the coronal and sagittal X-ray images. Alternatively, the lines or curves are drawn by replacing existing pixels of the coronal and sagittal X-ray images with replacement pixels of a predetermined color, e.g., cyan or magenta. This process of drawing a line or curve may be done according to image processes known to those skilled in the art.

At block 1108, a three-dimensional model of a second spine is analyzed in view of the four-dimensional model of the first spine to determine parameters of the surgical device for the second spine. In some embodiments, the three-dimensional model of the second spine is also analyzed in view of medical data pertaining to both the first and second spines. For example, if the first and second spines are the same or similar in a preoperative state, and the medical data pertaining to both the first and second spines are similar, a prediction can be made that the first spine will behave similarly to the second spine during a postoperative period. Thus, the surgical device applied to the first spine may be adjusted to avoid any alignment issues that arise in the second spine during the postoperative period.

At block 1110, surgical device is constructed and deployed in the second spine based on the predictions made at block 1108 and based on parameters of the spinal column dimensions and needed surgical device.

Figure 12A:
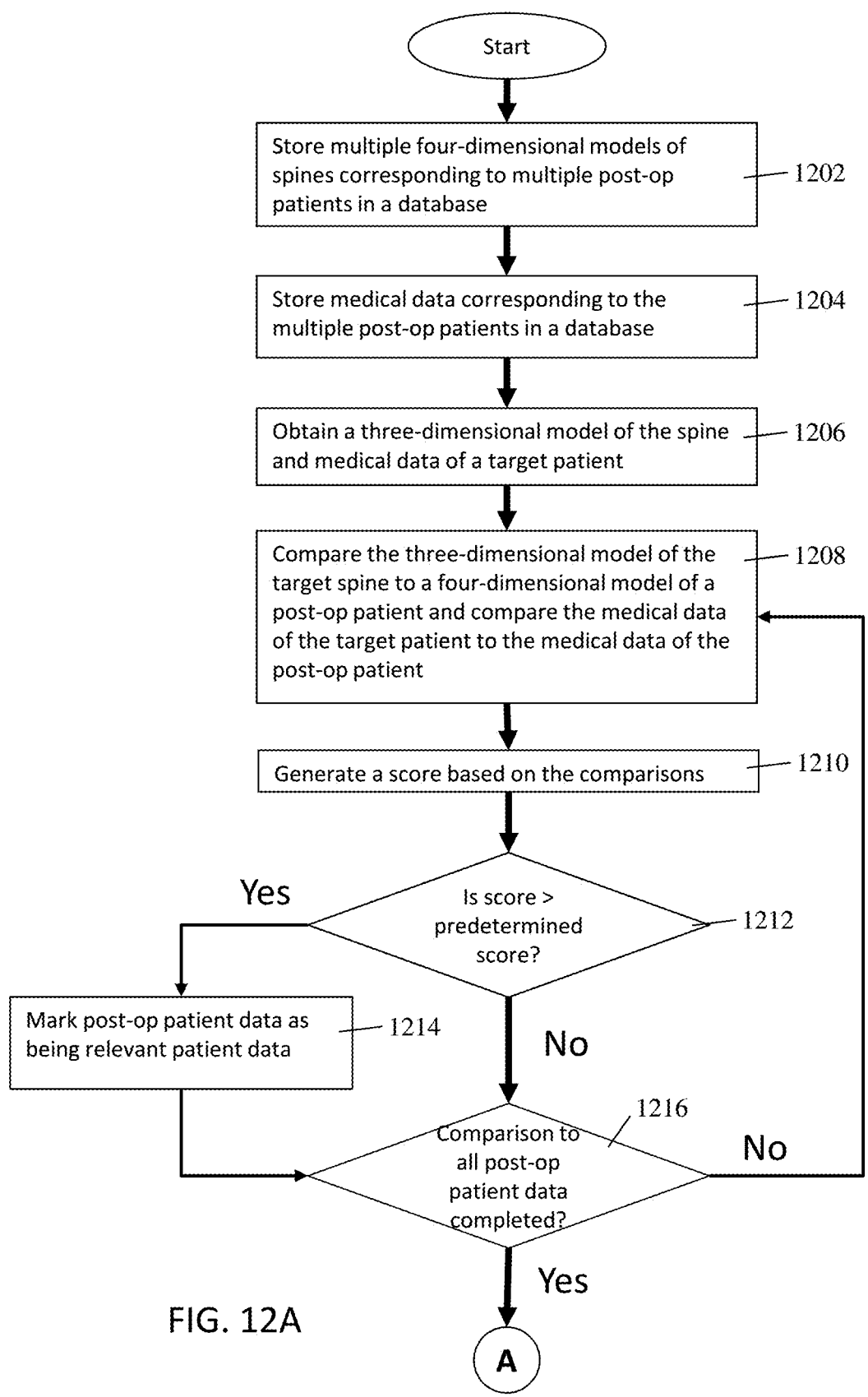
FIGS. 12A and 12B are flow diagrams illustrating a process for analyzing data from different patients and using that analysis to perform spinal surgery in accordance with some embodiments.
Figure 12B:
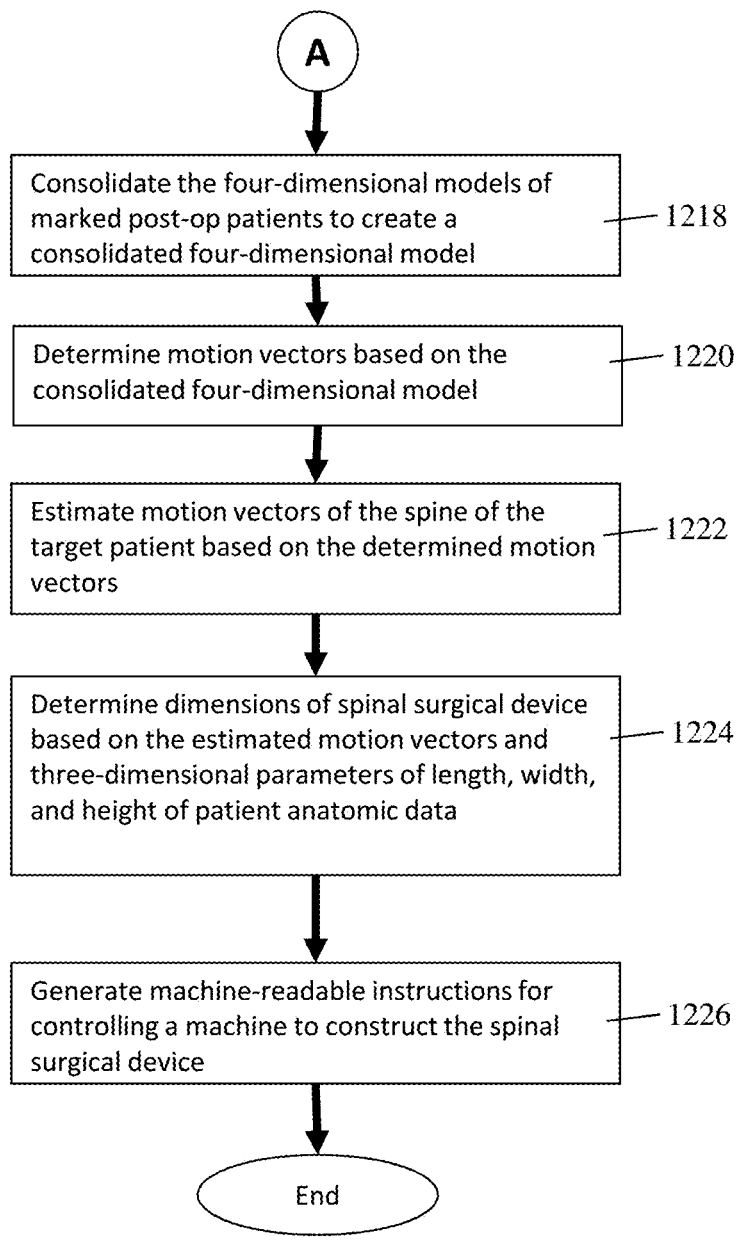

FIGS. 12A and 12B are flow diagrams illustrating a process for analyzing data from different patients and using that analysis to perform spinal surgery in accordance with some embodiments.

At block 1202, multiple four-dimensional models of spines corresponding to multiple postoperative patients are stored in a database. At block 1204, medical data corresponding to multiple postoperative patients is stored in a database as well. At block 1206, a three-dimensional model of the curvature of the spine and medical data of a target patient are obtained for analysis prior to a surgical procedure. At block 1208, the three-dimensional model of the target spine is compared to a four-dimensional model of the curvature of a spine of many postoperative patients and the medical data of the target patient is compared to the medical data of those post-operative patients. Then, at block 1210, a score may be generated based on the comparisons made between the models and between the medical data of the target patient and the postoperative patients.

For example, a higher score may be applied to a four-dimensional model that, in the preoperative state, most closely resembles the three-dimensional model of the target spine and the medical data of the target patient is closely related to the medical data of the postoperative patient. In embodiments, one score may be generated based on the comparison of the models and another score may be generated based on the comparison of the medical data.

At block 1212, the computer determines whether the score is greater than a predetermined score. If the score is greater than a predetermined score, the postoperative patient data is marked as being relevant patient data at block 1214. At block 1216, the computer determines whether comparisons have been completed for all postoperative patient data. If there is more post-op patient data, the process returns to step 1208 to compare models and medical data of the patients. If the comparisons have been completed, the four-dimensional models of marked postoperative patients are consolidated to create a consolidated four-dimensional model.

At block 1220, motion vectors are determined based on the consolidated four-dimensional model. At block 1222, motion vectors of the spine of the target patient are estimated based on the determined motion vectors. Then, at block 1224, dimensions of a spinal surgical device are determined based on the estimated motion vectors of the spine of the target patient and three-dimensional parameters of length, width, and height of patient anatomic data. At block 1226, machine-readable instructions for controlling a machine to construct the spinal surgical device are generated and are transmitted to the machine. In this manner, a surgical device may be constructed that accounts for estimated vectors to ensure that the target patient's spine maintains coronal and sagittal balance during the postoperative period.

In embodiments, the movement of the spine may be predicted using a model. In embodiments, the shape of a spine, whether it is normal or is deformed, can be defined by a mathematical equation. These equations can be modeled statistically using a spline or a non-linear regression.

For example, a normal spine is made up of two, connected, logistic ogives, which are also known as sigmoidal or S-shaped curves. The ogives may take the following form:

$$Y=1/(1+e^{(\beta^*(\tau-x))})$$

The spline may be the easiest curve to fit and may provide useful information. The nonlinear regression provides more information, which, in certain applications, may be better.

Predictive analytics comes into play when the relevant medical data for a patient is known before the surgery. The relevant medical data may include the diagnosis, cobb angle, and/or Lenke classification. Then, a cohort of patients is found in a database that have the same or similar characteristic medical data.

For example, a new patient may be diagnosed with Adolescent Idiopathic Scoliosis (AIS) and a Lenke 1A curve. Before surgery, the relevant medical data for the new patient is known. In the database, there may be a number of old patients (e.g., 100 old patients) with AIS and Lenke 1A curves having the same or similar characteristic medical data. The medical data of the old patients in the database may include, among other medical data, the following:
  The surgical approach (Posterior versus Anterior versus Lateral)
  Levels fused, for example, T2 to T11, etc.
  Type and size of hardware implanted (e.g., 5.5 mm rods, 6.5 mm screws; Titanium, Stainless steel)
  Operative time, blood loss, fluoroscope imaging time, ligaments resected, etc.
  Follow-up information, complications, Health Related Quality of Life (HRQoL) scores Some or all of this medical data (which may be represented as variables) may be combined together using Boolean logic (e.g., AND, OR, NOT) as predictors to the new patient and factored in as probability functions. Then, an outcome metric is determined or chosen. For example, if global balance (which means head-over-pelvis) AND posterior surgical approach AND thoraco-lumbar junction was crossed AND titanium hardware (screws and rods) were used NOT (pelvic tilt (this measure was irrelevant) OR blood loss (did not matter)), the probability of success of the surgery for the new patient may be 92.4%. But if the transverse ligament is cut on the concave side (intraoperative data), the probability of success of the surgery for the new patient may drop to 73.5%. In embodiments, some or all of the relevant medical data may be used to predict movement of the new patient's spine after surgery, which, in turn, may be used to determine the probability of success of the surgery performed on the new patient's spine.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto. For example, while the present disclosure makes reference to the spine, the present disclosure contemplates application of the systems and methods to other types of bony structures, such as bony structures in an arm, hand, leg, or foot.

The invention claimed is:

1. A method, comprising:
  obtaining a first X-ray image of at least a portion of a spine in a first plane;
  obtaining a second X-ray image of the at least a portion of a spine in a second plane;
  drawing a line through vertebral bodies of the at least a portion of a spine in the first X-ray image and in the second X-ray image;
  constructing a three-dimensional model based on the lines drawn on the first and second X-ray images;
  acquiring medical data regarding a patient;
  predicting, based on the three-dimensional model in view of the medical data, postoperative changes to movement of the spine over time, wherein the predicted postoperative changes include a first predicted postoperative change to movement of the spine at a first time and one or more additional predicted postoperative changes at times subsequent to the first time; and
  determining parameters of a spinal device based on the predicted movement of the spine including the first predicted postoperative change to movement of the spine at the first time and the one or more additional predicted postoperative changes.

2. The method of claim 1, wherein the spinal device is a screw, a rod, a cervical plate, a spine implant, an interbody device, or an artificial disc.

3. The method of claim 1, wherein the first plane is a coronal plane and the second plane is a sagittal plane.

4. The method of claim 1, further comprising obtaining a third X-ray image of the at least a portion of a spine in an axial plane, wherein constructing the three-dimensional model includes constructing the three-dimensional model based on the lines drawn on the first, second, and third X-ray images.

5. The method of claim 1, wherein the method further comprises:
identifying a line on the first X-ray image; and
identifying a line on the second X-ray image.

6. The method of claim 5, wherein the line on the first X-ray image and the line on the second X-ray image are colored lines, wherein identifying the colored lines includes quantifying the color of the colored lines and identifying differences in characteristics of the colored lines,
wherein the color of the colored lines includes at least one of red, green, or blue, and
wherein the characteristics include at least one of intensity, hue, saturation, contrast, or brightness.

7. The method of claim 1, further comprising calibrating the first X-ray image and the second X-ray image.

8. The method of claim 1, further comprising obtaining coronal Y-Z coordinates or pixels of a central vertebral line with vertebral bodies and discs identified; and
obtaining sagittal X-Z coordinates or pixels.

9. The method of claim 1, further comprising compensating for differences in magnification between the first X-ray image and the second X-ray image; and
scaling the first and second X-ray images.

10. The method of claim 1, further comprising combining the first and second X-ray images to construct the three-dimensional model.

11. The method of claim 10, further comprising:
obtaining at least one four-dimensional model for a similar spine;
analyzing the three-dimensional model based on the at least one four-dimensional model to predict movement of the spine; and
determining the parameters of the spinal device based on the predicted movement of the spine.

12. The method of claim 11, wherein the similar spine is an abnormal spine, and
wherein the spine is a one-level degenerative disc case and the similar spine is a two-level degenerative disc case.

13. The method of claim 1, wherein the medical data includes at least one of diagnosis information, operative information, follow-up information, quality of life score, cardia information, diabetes information, radiographic information, or intra-operative information.

14. The method of claim 13, wherein the quality of life score is selected from the group consisting of Visual Analog Scale (VAS), Oswestry Disability Index (ODI), Neck Disability Index, Rowland-Morris, Short Form Health Survey-12, Short Form Health Survey-36, Scoliosis Research Society-36 (SRS36), and Scoliosis Research Society-22 (SRS-22).

15. The method of claim 1, generating instructions to construct the spinal device with a three-dimensional printer based on the parameters of the spinal device.

16. A method for performing spinal surgery, comprising:
obtaining, over a predetermined period, a plurality of first images of at least a portion of a first spine in a first plane;
obtaining, over a predetermined period, a plurality of second images of at least a portion of the first spine in a second plane;
drawing a line through vertebral bodies of the at least the portion of the first spine in the plurality of first images and in the plurality of second images;
acquiring medical data relating to the first spine;
constructing a four-dimensional model based on the lines drawn on the plurality of first and second images;
predicting, based on the four-dimensional model in view of the medical data, postoperative changes to movement of the first spine over time, wherein the predicted postoperative changes include a first predicted postoperative change to movement of the spine at a first time and one or more additional predicted postoperative changes at times subsequent to the first time; and
determining parameters of a spinal device based on the four-dimensional model and the obtained medical data, and the predicted movement of the spine, including the first predicted postoperative change to movement of the spine at the first time and the one or more additional predicted postoperative changes.

17. A method of performing a surgical procedure, comprising:
obtaining, over a predetermined period, a plurality of first images of a first plurality of skeletal bodies in a first plane;
obtaining, over a predetermined period, a plurality of second images of the first plurality of skeletal bodies in a second plane;
drawing a line through the first plurality of skeletal bodies in the plurality of first and second images;
constructing a three-dimensional model based on the lines drawn on the plurality of first and second images;
predicting postoperative changes to movement of the spine over time based on the three-dimensional model and the medical data, wherein the predicted postoperative changes include a first predicted postoperative change to movement of the spine at a first time and one or more additional predicted postoperative changes at times subsequent to the first time; and
determining parameters of a medical device based on the predicted movement of the spine including the first predicted postoperative change to movement of the spine at the first time and the one or more additional predicted postoperative changes.

18. The method of claim 17, wherein the first and second plurality of skeletal bodies include bones of and/or associated with a hip, knee, or ankle.

19. A system for manufacturing a spinal device, comprising:
server that stores medical data;
an X-ray apparatus that captures a first X-ray image of a spine in a first plane and a second X-ray image of the spine in a second plane, and stores the first and second X-ray images in the server;
a computer including:
a communications interface;
one or more processors coupled to the communications interface; and
a memory coupled to the one or more processor and having stored thereon instructions which, when executed by the one or more processors, causes the one or more processors to:
acquire via the communications interface the first X-ray image of the spine in the first plane and the second X-ray image of the spine in the second plane from the server;

store the first and second X-ray images in the memory; acquire medical data relating to the spine from the server; store the medical data in memory;

draw, on the first X-ray image and the second X-ray image, a curve through vertebral bodies of the spine;

determine coordinates of the spine by detecting the curve on the first X-ray image and the second X-ray image;

construct a three-dimensional model based on the curves on the first and second X-ray images;

predict movement of the spine during a postoperative period based on the three-dimensional model and the medical data, which includes three-dimensional models of other spines;

determine parameters of a spinal device based on the predicted movement of the spine; and transmit via the communications interface commands or instructions for forming a surgical device having the determined parameters; and a three-dimensional printer or milling machine that acquires the commands or instructions and forms the surgical device based on the commands or instructions.

* * * * *